United States Patent [19]

Forni et al.

[11] 4,022,840

[45] May 10, 1977

[54] PROCESS AND CATALYST FOR THE PREPARATION OF LINEAR MONO-OLEFINES BY CATALYTIC DEHYDROGENATION OF LINEAR PARAFFINS

[75] Inventors: Lucio Forni; Renzo Invernizzi, both of Milan, Italy

[73] Assignee: Societa' Italiana Resine S.I.R. S.p.A., Milan, Italy

[22] Filed: May 23, 1975

[21] Appl. No.: 580,233

[30] Foreign Application Priority Data

May 30, 1974 Italy .................................. 23316/74

[52] U.S. Cl. .............................. 260/683.3; 252/473
[51] Int. Cl.² ........................................... C07C 5/18
[58] Field of Search ................. 260/683.3; 252/473

[56] References Cited

UNITED STATES PATENTS

| | | | |
|---|---|---|---|
| 2,030,283 | 2/1936 | De Rewal | 252/473 |
| 2,418,889 | 4/1947 | Kearby | 252/473 |
| 2,442,131 | 5/1948 | Kearby | 252/473 |
| 2,636,819 | 4/1953 | Streicher | 252/473 |
| 3,315,008 | 4/1967 | Abell et al. | 260/683.3 |
| 3,696,167 | 10/1972 | Juquin et al. | 260/683.3 |

*Primary Examiner*—Veronica O'Keefe
*Attorney, Agent, or Firm*—McNenny, Pearne, Gordon, Gail, Dickinson & Schiller

[57] ABSTRACT

Linear mono-olefines are prepared by contacting linear paraffins having from 6 to 16 carbon atoms per molecule with a porous dehydrogenation catalyst comprising beryllium oxide as a support and from 0.01 to 10% by weight of noble metal as active component.

8 Claims, No Drawings

PROCESS AND CATALYST FOR THE PREPARATION OF LINEAR MONO-OLEFINES BY CATALYTIC DEHYDROGENATION OF LINEAR PARAFFINS

The present invention relates to the production of linear mono-olefines having from 6 to 16 carbon atoms per molecule, by means of catalytic dehydrogenation, in the presence of hydrogen gas, of the corresponding linear parraffins having the same number of carbon atoms per molecule.

The linear mono-olefines having a relatively high number of carbon atoms in their molecules find many practical applications. Thus, for example, those having approximately 12 carbon atoms are used in the production of alkylbenzenes with a linear alkyl chain, which are valuable intermediate products in the manufacture of biologically degradable detergents.

Processes are known in the prior art for the preparation of linear mono-olefines by catalytic dehydrogenation of the corresponding linear paraffins. For this purpose, a flow formed by hydrogen gas and by a linear paraffin, or a mixture of linear paraffins, is put into contact with a dehydrogenation catalyst, operating at elevated temperature and at a pressure equal to or higher than atmospheric.

Catalysts suitable for this purpose are in general formed by platinum deposited on a support such as: silica and/or alumina and natural or synthetic alumino-silicates, the latter being commonly known as molecular sieves.

Other known catalysts are formed by alumina as a support and titanium oxide, platinum and arsenic, copper, cobalt molybdate or cobalt thiomolybdate as catalytically active materials. Under the conditions in which said catalysts disply their dehydrogenation activity, various secondary reactions occur, such as, for example: pyrolysis, isomerization and cyclization. Moreover, the secondary dehydrogenation reactions which occur frequently give rise to the formation of products having a degree of unsaturation higher than that of the mono-olefins, such as, for example, diolefines. Finally, coke deposits are frequently formed during the dehydrogenation reaction, which has the effect of limiting the life of the catalyst and its use on an industrial scale.

It is thought that the catalyst supports used in the prior art, especially silica, alumina and aluminosilicates, favour the secondary reactions which accompany the main reaction of formation of the mono-olefines.

In practice, however, in spite of the refinements introduced in the preparation of the catalyst, such as, for example, the treatment of the support with basic substances in order to reduce its surface acidity, the dehydrogenation processes of the prior art rarely achieve a selectivity of more than 90% in moles for the linear mono-olefines produced, said selectivity being normally between 50 and 85% in moles with respect to the moles of linear paraffins converted.

All this involves a loss of useful products and makes it necessary to adopt complex treatments for the purification and the recovery of the linear mono-olefins from the reaction products.

The aforesaid disadvantages are overcome, or at least greatly reduced, if the linear paraffins are dehydrogenated by the process of the present invention.

Therefore, an object of the present invention is to provide a process for the transformation of linear paraffins into linear mono-olefines which makes use of a dehydrogenation catalyst which is highly active and selective in said process and endowed with good mechanical characteristics.

Thus, the invention provides a process for the preparation of linear mono-olefines having from 6 to 16 carbon atoms per molecule by catalytic dehydrogenation of linear paraffins having from 6 to 16 carbon atoms per molecule, in the presence of hydrogen gas, at elevated temperature and at a pressure equal to or above atmospheric, characterized by contacting at least one of said paraffins with a porous dehydrogenation catalyst formed by beryllium oxide as a support and containing from 0.001 to 10% by weight of noble metal, prepared by:

co-precipitating hydroxides of beryllium and of at least one noble metal from an aqueous solution of soluble compounds of the said elements, the relative proportions of said compounds in said solution being such as to ensure in the finished catalyst a content of noble metal of from 0.001 to 10% by weight;

drying said hydroxides progressively for a period of at least 10 hours up to a temperature not exceeding about 150° C;

activating the resulting dried product at a temperature of from 100° to 600° C, first in an inert atmosphere for a period of at least 30 minutes and then in a reducing atmosphere for a period of at least 3 hours, and cooling the activated product in an inert atmosphere.

The following noble metals may be used: platinum, palladium, gold, iridium, ruthenium, rhodium and osmium.

The compounds of beryllium and of the noble metals which are used in the preparation of the catalyst, are those soluble in water and which give a precipitate of hydroxides of beryllium and noble metal, by the addition to the said solution of a precipitating agent such as, for example, alkali metal or ammonium hydrates.

Examples of beryllium compounds: nitrate, basic carbonate, oxalate.

Examples of compounds of the noble metals are: hexachloroplatinic acid, hexachloroiridic acid, chloroauric acid, tetrammineplatinum hydroxide, diammineplatinum dinitrite, tetramminepalladium hydroxide, ruthenium acetate, ruthenium acetylacetonate.

Preferably, said compounds are dissolved in water up to a total maximum concentration of the compounds of the order of 30% by weight and then an alkali metal or ammonium hydrate is added, bringing the pH of the resulting solution to a value in the range from 7 to 11. The hydroxides thus precipitated are separated and thoroughly washed with water.

It is also possible, but not convenient to perform the precipitation in a non-aqueous medium, for example in an alcoholic medium.

In any case the hydroxides are dried progressively for a period of at least 10 hours, although it is not convenient to exceed 50 hours. During drying the temperature must not exceed about 150° C.

The dried product is then activated, at a temperature of from 100° to 600° C and preferably from 150° to 500° C, first in an inert atmosphere, for example in a nitrogen atmosphere. After a period of at least 30 minutes and generally not more than 20 hours, the inert atmosphere is substituted by a reducing atmosphere, in general hydrogen, and the product is kept in such conditions for at least 3 hours, although it is not convenient to exceed 24 hours. Finally, it is cooled in an inert atmosphere.

In this way one obtains the catalyst in pulverulent form, which can be used such as it is in the process of the invention, or said powder can be pressed before use into the form of regular granules of requisite dimensions.

The catalyst is formed by beryllium oxide as a support and contains noble metal in a proportion of from 0.001 to 10% and preferably from 0.05 to 5% by weight. Optimum results are obtained with a proportion of noble metal from 0.1 to 1% by weight with respect to the weight of the catalyst.

As already stated one can utilize only one noble metal, or several noble metals, as the active part of the catalyst. Particularly good results are obtained by using the following pairs of metals: platinum-gold, platinumiridium and platinum-palladium.

The catalyst has typically the following other characteristics:

Surface area of the order of 100m$^2$/gram, porosity of the order of 0.25 ml/gram, at least 80% of the pores, and in general about 90% of them having a radius of from 20 to 30 Angstrom.

It is thought that the particularly good results obtainable by using the said catalyst in the process of the present invention are attributable to the nature of the support used, to the perfect distribution of the catalytically active metal on the said support and to the other characteristics, in particular to the distribution of the radii of the pores within a very restricted range of values.

In the preparation of the linear mono-olefines by the process of the present invention a mixture formed by linear paraffins and hydrogen gas is put into contact with the catalyst, normally in the form of a fixed bed, operating at elevated temperature and at atmospheric pressure or a pressure higher than atmospheric.

The temperature at which the process of the invention is carried out is normally included in a range of values from 350° to 650° C, and preferably from 400° to 550° C. The process is usually carried out at atmospheric pressure, although it is possible to operate at a pressure of several atmospheres, for example up to 10 atmospheres.

The linear paraffins are generally fed at a rate of from 0.001 to 100 volumes (calculated as a liquid) per hour for each volume of catalyst. Moreover, since the dehydrogenation reaction takes place in the presence of hydrogen gas, it is convenient to maintain the molar ratio of hydrogen to linear paraffin in the feed mixture at a value of from 1:1 to 50:1.

Operating under these conditions, a conversion of up to 30% in moles with respect to the linear paraffins supplied is achieved. Moreover, the selectivity for the linear mono-olefine is in each case equal to or greater than 90% in moles with respect to the moles of linear paraffins converted, and normally of the order of 95% in moles.

The catalyst has therefore a high activity in the dehydrogenation processes of the linear paraffins and a high selectivity for the linear mono-olefines produced. Consequently, the production of those by-products, derived from the secondary reactions, which constitute a disadvantage of the process of the prior art, is reduced to a minimum. As a result the treatments required for the purification and separation of the linear mono-olefines produced are greatly simplified.

Finally, the almost complete absence of coke formation in the process, together with the good mechanical characteristics of the catalyst, allow the use of said catalyst in the process of the invention for industrially useful periods.

The following experimental examples will serve to illustrate this invention without limiting it in any way.

EXAMPLE 1

To 41 grams of beryllium nitrate tetrahydrate are added 8.31 grams of ammonium nitrate together with hexachloroplatinic and hexachloroiridic acid. The latter compounds are added in the form of a solution and in such quantities as to ensure in the finished catalyst a quantity of metallic platinum equal to 0.3–0.5% by weight and a quantity of metallic iridium equal to 0.05–0.15% by weight. To the mixture thus obtained are added 100 ml of water and the resulting solution is brought to ebullition.

To the boiling and stirred solution one adds drop by drop an ammoniacal aqueous solution at 30% by weight, until the pH of the solution is equal to about 9.

In this way a precipitate is formed consisting essentially of hydroxides of beryllium, platinum and iridium.

The precipitate thus formed is filtered and washed with 250 ml of boiling water.

It is then allowed to dry on water bath and calcined in a drying oven for 12 hours at 150°–160° C and then in an oven at 470° C for 30 minutes under a weak current of nitrogen. The solid thus obtained is brought to 500° C in the nitrogen atmosphere and then treated in a hydrogen current, at the said temperature for 5 hours. Finally, it is cooled at room temperature in a nitrogen atmosphere.

In this way a catalyst having the following composition is obtained:

beryllium oxide : 99.5% by weight
platinum : 0.4% by weight
iridium : 0.1% by weight The said catalyst has furthermore a specific surface area of about 100 m$^2$/gram, a pore volume equal to 0.26 ml/gram, about 90% of the pores having a radius from 20 to 30 Angstrom.

EXAMPLE 2

The catalyst obtained in the manner described in Example 1 is used for dehydrogenating n-dodecane, as follows.

The said catalyst is arranged in the form of a fixed bed in a tubular reactor. The dehydrogenation is carried out in the reactor continuously, operating at 450° C and at atmospheric pressure, feeding the head of the reactor with n-dodecane and hydrogen.

In particular the n-dodecane is fed at a rate of 1 volume (calculated as a liquid) per hour for each volume of catalyst, while maintaining a molar ratio between the hydrogen and the n-dodecane of 12:1.

Operating under these conditions the coversion of the n-dodecane is of 22.1% in moles. Moreover, the selectivity for the linear dodecene is of 94% in moles with respect to the moles of n-dodecane converted.

EXAMPLE 3

A catalyst having the following composition is prepared according to the procedure described in Example 1: beryllium oxide 99.5% by weight and platinum 0.5% by weight.

The catalyst is used to dehydrogenate n-dodecane under the conditions of Example 2, and a conversion of 22.7% in moles with a selectivity for the n-dodecene of 95% in moles is obtained.

EXAMPLE 4

A catalyst having the following composition is prepared according to the procedure described in Example 1: beryllium oxide 99.5% by weight, platinum and iridium 0.5% by weight (atomic ratio of platinum to iridium = 3:1).

The catalyst is used to dehydrogenate n-dodecane under the conditions of Example 2, and a conversion of 19.9% in moles with a selectivity for the n-dodecene of 94% in moles is obtained.

EXAMPLE 5

The catalyst prepared as described in Example 1 is used to dehydrogenate n-dodecane, operating at 470° C, using a molar ratio of hydrogen to n-dodecane of 4:1, the other conditions being identical to those of Example 2.

There is obtained in this way a of conversion of 30% in moles with a selectivity for the n-dodecene of 90% in moles.

EXAMPLE 6

The catalyst prepared as described in Example 1 is used to dehydrogenate n-dodecane using a molar ratio of hydrogen to n-dodecane of 20:1, the other conditions being identical to those of Example 2.

In a run of 270 hours a conversion of 12% in moles with a selectivity for the n-dodecene of 95% in moles is obtained.

EXAMPLE 7

The catalyst prepared as described in Example 1 is used to dehydrogenate n-dodecane at 435° C, the other conditions being the same as those of Example 2.

After a one hour run a conversion of 16% in moles with a selectivity for the n-dodecene of 94% in moles is noted. After a 380 hours run a conversion of 11% in moles with a selectivity in n-dodecene of 94% in moles is noted. The catalyst is regenerated and reused for 100 hours and this for two consecutive times.

The regeneration is effected by feeding to the catalyst a mixture of oxygen and nitrogen with a volumetric proportion of oxygen which in 5 hours passes gradually from 1% initially to 21% finally while the temperature is maintained at 500° C.

After every regeneration the values of the conversion and of the selectivity return to the original ones obtained with the fresh catalyst.

We claim:

1. A process for the preparation of linear mono-olefines having from 6 to 16 carbon atoms per molecule by catalytic dehydrogenation of linear paraffins having from 6 to 16 carbon atoms per molecule, which comprises contacting in the presence of hydrogen gas, at elevated temperature and at a pressure equal to or above atmospheric, at least one of said paraffins with a porous dehydrogenation catalyst consisting essentially of beryllium oxide and of from 0.001 to 10% by weight of at least one noble metal, prepared by:

co-precipitating hydroxides of beryllium and of at least one noble metal from an aqueous solution of soluble compounds of the said elements, the relative proportions of said compounds in said solution being such as to ensure in the finished catalyst a content of noble metal of from 0.001 to 10% by weight;

drying said hydroxides progressively for a period of at least 10 hours up to a temperature not exceeding about 150° C;

activating the resulting dried product at a temperature of from 100° to 600° C, first in an inert atmosphere for a period of at least 30 minutes and then in a reducing atmosphere for a period of at least 3 hours;

cooling the activated product in an inert atmosphere.

2. The process of claim 1, wherein said content of noble metal in the catalyst is from 0.05 to 5% by weight.

3. The process of claim 1, wherein said catalyst has a specific surface area of the order of 100 m$^2$/g, a pore volume of the order of 0.25 ml/g, at least 80% of the pores having a radius of from 20 to 30 A.

4. The process of claim 1, wherein said noble metal is selected in the group consisting of platinum, palladium, gold, iridium, ruthenium, rhodium and osmium.

5. The process of claim 1, wherein said hydroxides are co-precipitated by bringing said solution to a pH value of from 7 to 11 by addition of an alkali metal or ammonium hydroxide.

6. The process of claim 1, wherein said hydroxides are dried for a period of from 10 to 50 hours.

7. The process of claim 1, wherein said product is activated at a temperature of from 150° to 500° C, first in said inert atmosphere for a period of from 30 minutes to 20 hours and then in said reducing atmosphere for a period of from 3 to 24 hours.

8. The process of claim 7, wherein said reducing atmosphere is a hydrogen atmosphere.

* * * * *